United States Patent [19]
Bordas-Nagy et al.

[11] Patent Number: 6,013,827
[45] Date of Patent: Jan. 11, 2000

[54] COMPOUNDS

[75] Inventors: Joseph Bordas-Nagy, Sunnyvale, Calif.; Peter Gorycki, Conshohocken; Kevin Scott Webb, Phoenixville, both of Pa.

[73] Assignee: SmithKline Beecham Corporation, Philadelphia, Pa.

[21] Appl. No.: 08/424,327

[22] PCT Filed: Mar. 8, 1995

[86] PCT No.: PCT/US95/02965

§ 371 Date: Sep. 11, 1996

§ 102(e) Date: Sep. 11, 1996

[87] PCT Pub. No.: WO95/24381

PCT Pub. Date: Sep. 14, 1995

[51] Int. Cl.⁷ .................................................. C07C 255/00
[52] U.S. Cl. ...................... 558/406; 514/520; 514/521; 514/523; 560/21; 560/27; 560/59; 562/469; 564/171
[58] Field of Search ............................ 558/406; 560/21, 560/27, 59; 562/469; 564/171

[56] References Cited

U.S. PATENT DOCUMENTS 4,065,573  12/1977  Lednicer .

FOREIGN PATENT DOCUMENTS

WO 93/19749  10/1993  WIPO .
WO 93/19750  10/1993  WIPO .
WO 93/19751  10/1993  WIPO .

OTHER PUBLICATIONS

Chemical Abstracts, vol. 120, Issued 1994, Christensen, *Cyclohexylbenzene* . . . No. 120: 134020m.

Chemical Abstracts, vol. 120, Issued 1994, Christensen, *Preparation of* . . . No. 120: 163532k.

Chemical Abstracts, vol. 120, Issued 1994, Christensen, *Cyclohexylbenzones* . . . No. 120: 191326q.

*Primary Examiner*—Paul J. Killos
*Attorney, Agent, or Firm*—James M. Kanagy; Charles M. Kinzig

[57] ABSTRACT

This invention relates to componds of formula I

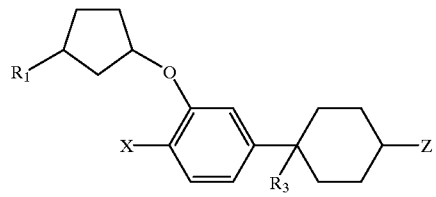

which are useful as PDE IV inhibitors and for treating diseases related thereto.

9 Claims, No Drawings

COMPOUNDS

FIELD OF THE INVENTION

The present invention relates to novel phenylcyclohexan-1-ylcarboxylic acids, pharmaceutical compositions containing these compounds, the use of these compounds in treating allergic and inflammatory diseases and to the use of these compounds to inhibit the production of Tumor Necrosis Factor (TNF).

BACKGROUND OF THE INVENTION

Bronchial asthma is a complex, multifactorial disease characterized by reversible narrowing of the airway and hyperreactivity of the respiratory tract to external stimuli. Identification of novel therapeutic agents for asthma is made difficult by the fact that multiple mediators are responsible for the development of the disease. Thus, it seems unlikely that eliminating the effects of a single mediator will have a substantial effect on all components of chronic bronchial asthma.

An alternative to the "mediator approach" is to regulate the activity of cells responsible for the pathophysiology of asthma. Cyclic AMP (cAMP, adenosine cyclic 3',5'-monophosphate) modulates the activity of most, if not all, of the cells that contribute to the pathophysiology of extrinsic (allergic) asthma. An elevation of cAMP would produce beneficial effects including: (1) airway smooth muscle relaxation, (2) inhibition of mast cell mediator release, (3) suppression of neutrophil degranulation, (4) inhibition of basophil degranulation, and (5) inhibition of monocyte and macrophage activation. Cyclic AMP has been shown to mediate cellular responses to a wide range of hormones, neurotransmitters and drugs; [Krebs Endocrinology Proceedings of the 4th International Congress Excerpta Medica, 17–29, 1973].

One potential means to regulate the activity of cells responsible for the pathophysiology of asthma is to control the intracellular levels of cyclic AMP. Cellular cAMP levels are elevated when an appropriate agonist binds to particular cell surface receptors, thereby activating adenylate cyclase to convert $Mg^{+2}$-ATP to cAMP at an accelerated rate. The principal cellular mechanism for the inactivation of cAMP is hydrolysis of the 3'-phosphodiester bond by one or more of a family of isozymes referred to as cyclic nucleotide phosphodiesterases (cyclic nucleotide phosphodiesterase hereinafter "PDE"s). Hence, compounds that activate adenylate cyclase or inhibit phosphodiesterase should be effective in suppressing the inappropriate activation of airway smooth muscle and a wide variety of inflammatory cells.

It has been shown that a distinct PDE isozyme, PDE IV, is responsible for cAMP breakdown in airway smooth muscle and inflammatory cells. [Torphy, "Phosphodiesterase Isozymes: Potential Targets for Novel Anti-asthmatic Agents" in New Drugs for Asthma, Barnes, ed. IBC Technical Services Ltd., 1989]. Research indicates that inhibition of this enzyme not only produces airway smooth muscle relaxation, but also suppresses degranulation of mast cells, basophils and neutrophils along with inhibiting the activation of monocytes and neutrophils. The beneficial effects of PDE IV inhibition are markedly potentiated when adenylate cyclase activity of target cells is elevated by appropriate hormones or autocoids. Thus, PDE IV inhibitors would be effective in the asthmatic lung, where levels of prostaglandin $E_2$ and prostacyclin (both activators of adenylate cyclase) are elevated. PDE IV inhibitors offer a unique approach to the pharmacotherapy of bronchial asthma, and possess significant therapeutic advantages over agents currently on the market The compounds of this invention have the ability to inhibit PDE IV.

The compounds of this invention also inhibit the production of TNF, a serum glycoprotein. Excessive or unregulated TNF production has been implicated in mediating or exacerbating a number of undesirable physiological conditions, such as diseases, and including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, human acquired immune deficiency syndrome (ADS), cachexia secondary to AIDS, AIDS related complex (ARC), keloid formation, scar tissue formation, Crohn's disease, ulcerative colitis, or pyresis, in addition to a number of autoimmune diseases, such as multiple sclerosis, autoimmune diabetes and systemic lupus erythematosis.

AIDS results from the infection of T lymphocytes with Human Immunodeficiency Virus (HIV). At least three types or strains of HIV have been identified: HIV-1, HIV-2 and HIV-3. As a consequence of HIV infection, T-cell-mediated immunity is impaired and infected individuals manifest severe opportunistic infections and/or unusual neoplasms. HIV entry into a T lymphocyte requires prior T lymphocyte activation. Once an activated T lymphocyte has been infected with HIV, the T lymphocyte must be maintained in an activated state in order to permit HIV gene expression and/or HIV replication.

Cytokines, including TNF, are implicated in activated T-cell-mediated HIV protein expression and/or virus replication as playing a role in maintaining T lymphocyte activation. Therefore, interference with cytokine activity in an HIV-infected individual, such as by inhibition of TNF production, aids in limiting the maintenance of T cell activation, and thereby mitigates the progression of HIV infection to previously uninfected cells. When HIV infection of previously uninfected cells is diminished, a slowing or elimination of the progression of immune dysfunction caused by HIV infection results.

Monocytes, macrophages, and related cells, such as kupffer and glial cells, have also been implicated in the maintenance of HIV infection. These cells, like T cells, are targets for viral replication, where the level of viral replication is dependent upon the activation state of the cells. [See Rosenberg et al., The Immunopathogenesis of HIV Infection, Advances in Immunology, Vol. 57, 1989]. Monokines, such as TNF, have been shown to activate HIV replication in monocytes and/or macrophages [See Poli et al., Proc. Natl. Acad. Sci., 87:782–784, 1990], therefore, inhibition of monokine production or activity aids in limiting HIV progression as stated above for T cells.

TNF has also been implicated in various roles with other viral infections, such as the cytomegalovirus (CMV), influenza virus, adenovirus, and the herpes virus for similar reasons as those noted. TNF is also associated with yeast and fungal infections. Specifically *Candida albicans* has been shown to induce TNF production in vitro in human monocytes and natural killer cells. [See Riipi et al., Infection and Immunity, 58(9):2750–54, 1990; and Jafari et al., Journal of Infectious Diseases, 164:389–95, 1991. See also Wasan et

SUMMARY OF THE INVENTION

This invention relates to certain compounds of Formula I

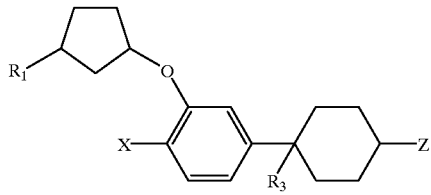

(I)

wherein $R_1$ is OH or an ether or ester thereof,

X is $YR_2$, halogen, nitro, $NR_4R_5$ or formyl amine;

Y is O or $S(O)_m$, where m is 0, 1 or 2;

$R_2$ is methyl or ethyl, where either methyl or ethyl may be optionally substituted by 1 or more halogens;

$R_3$ is hydrogen, halogen, $C_{1-4}$alkyl, $CH_2NHC(O)C(O)NH_2$, halo-substituted $C_{1-4}$alkyl, —CH=$CHR_{8'},R_8$, cyclopropl optionally subsituted by $R_{8'}$, CN, $OR_8$, $CH_2OR_8$, $NR_8R_{10}$, $CH_2NR_8R_{10}$, C(Z')H, $C(O)OR_8$, $C(O)NR_8R_{10}$, or —C≡$CR_8$;

$R_4$ and $R_5$ are independently hydrogen or $C_{1-2}$ alkyl;

$R_7$ is —$(CR_4R_5)_qR_{12}$ or $C_{1-6}$ alkyl wherein the $R_{12}$ or $C_{1-6}$ alkyl group is optionally substituted one or more times by $C_{1-2}$ alkyl optionally substituted by one to three groups selected from —F, —Br, —Cl, —$NO_2$, —$NR_{10}R_{11}$, —C(=O)$R_8$, —C(=O)$OR_8$, —$OR_8$, —CN, —C(=O)$NR_{10}R_{11}$, —OC(=O)$NR_{10}R_{11}$, —OC(=O)$R_8$, —$NR_{10}C$(=O)$NR_{10}R_{11}$, —$NR_{10}C$(=O)$R_{11}$, —$NR_{10}C$(=O)$OR_9$, —$NR_{10}C$(=O)$R_{13}$, —C(=$NR_{10}$)$NR_{10}R_{11}$, —C(=N— CN)$NR_{10}R_{11}$, —C(=N—CN)$SR_9$, —$NR_{10}C$(=N—CN)$NR_{10}R_{11}$, —$NR_{10}S$(=O)$_2R_9$, —$S(O)_{m'}R_9$, —$NR_{10}C$(=O)C(=O)$NR_{10}R_{11}$, —$NR_{10}C$(=O)C(=O)$R_{10}$, thiazolyl, imidazolyl, oxazolyl, pyrazolyl, triazolyl or tetrazolyl;

$R_8$ is —H or $R_9$;

$R_{8'}$ is $R_8$ or fluorine;

$R_9$ is $C_{1-4}$ alkyl optionally substituted by one to three —F;

$R_{10}$ is $OR_8$, hydrogen, or $C_{1-4}$alkyl optionally substituted by one to three fluorines;

$R_{11}$ is —H or $C_{1-4}$ alkyl optionally substituted by one to three —F; or when $R_{10}$ and $R_{11}$ are as $NR_{10}R_{11}$ they may together with the nitrogen form a 5 to 7 membered ring optionally containing at least one additional heteroatom selected from O, N or S;

$R_{12}$ is $C_{3-7}$ cycloalkyl, 2-pyridyl, 3-pyridyl, 4-pyridyl, pyrimidyl, pyrazolyl, 1-imidazolyl, 2-imidazolyl, thiazolyl, triazolyl, pyrrolyl, piperazinyl, piperidinyl, morpholinyl, furanyl, 2-thienyl, 3-thienyl, 4-thiazolyl, 5-thiazolyl, quinolinyl, naphthyl or phenyl;

$R_{13}$ is a heterocyclic ring selected from oxazolidinyl, oxazolyl, thiazolyl, pyrazolyl, triazolyl, tetrazolyl, imidazolyl, imidazolidinyl, thiazolidinyl, isoxazolyl, oxadiazolyl or thiadiazolyl, where $R_{13}$ is appended to a compound of Formula (I) through a carbon atom of the heterocyclic ring, and where each heterocyclic ring may be unsubstituted or substituted by one or two $C_{1-2}$ alkyl groups;

$R_{14}$ is H or $R_7$, or when $R_{10}$ and $R_{14}$ are as $NR_{10}R_{14}$, they may together with the nitrogen atom form a 5 to 7 membered ring optionally containing at least one additional heteroatom selected from O, N or S;

m' is 0, 1 or 2;

q is 0, 1 or 2.

Y' is O or S;

Z is C(=Y')$R_{14}$, C(=O)$OR_{14}$, C(=Y')$NR_{10}R_{14}$, C(=$NR_{10}$)$NR_{10}R_{14}$, CN, C(=$NOR_8$)$R_{14}$, C(=O)$NR_8NR_8C$(=O)$R_8$, C(=O)$NR_8NR_{10}R_{14}$, C(=$NOR_{14}$)$R_8$, C(=$NR_8$)$NR_{10}R_{14}$, C(=$NR_{14}$)$NR_8R_8$, C(=N—CN)$NR_{10}R_{14}$, C(=N—CN)$SR_9$, 2-imidazolyl, 4-imidazolyl, 5-imidazolyl, 3-pyrazolyl, 4-pyrazolyl, 5-pyrazolyl, 4-triazolyl[1,2,3], 5-triazolyl [1,2,3], 3-triazolyl[1,2,4], 5-triazolyl[1,2,4], 5-tetrazolyl, 2-oxazolyl, 4-oxazolyl, 5-oxazolyl, 3-isoxazolyl, 4-isoxazolyl, 5-isoxazolyl, 3-oxadiazolyl [1,2,4], 5-oxadiazolyl[1,2,4], 2-oxadiazolyl[1,3,4], 2-thiadiazolyl[1,3,4], 2-thiazolyl, 4-thiazolyl, 5-thiazolyl, 2-oxazolidinyl, 4-oxazolidinyl, 5-oxazolidinyl, 2-thiazolidinyl, 4-thiazolidinyl or 5-thiazolidinyl, 2-imidazolidinyl, 4-imidazolidinyl, or 5-imidazolidinyl; wherein all of the heterocyclic ring systems may be optionally substituted one or more times by $R_{14}$;

Z' is O, $NR_9$, $NOR_8$, NCN, C(—CN)$_2$, $R_8CN$, $CR_8NO_2$, $CR_8C$(O)$OR_8$, $CR_8C$(O)$NR_8R_8$, C(—CN)$NO_2$, C(—CN)C(O)$OR_9$, or C(—CN)C(O)$NR_8R_8$; or a pharmaceutically acceptable salt thereof.

This invention also relates to pharmaceutical compositions comprising a compound of Formula (I) and a pharmaceutically acceptable excipient.

This invention also relates to a method of mediation or inhibition of the enzymatic activity (or catalytic activity) of PDE IV in mammals, including humans, which comprises administering to a mammal in need thereof an effective amount of a compound of Formula (I) or a pharmaceutically acceptable salt thereof.

This invention also relates to a method for the treatment of allergic and inflammatory disease which comprises administering to a mammal, including humans, in need thereof, an effective amount of a compound of Formula (I) or a pharmaceutically acceptable salt thereof.

This invention also relates to a method for the treatment of asthma which comprises administering to a mammal, including humans, in need thereof, an effective amount of a compound of Formula (I) or a pharmaceutically acceptable salt thereof.

This invention further relates to a method of inhibiting TNF production in a mammal, including humans, which comprises administering to a mammal in need of such treatment, an effective TNF inhibiting amount of a compound of Formula (I) or a pharmaceutically acceptable salt thereof. This method may be used for the prophylactic treatment or prevention of certain TNF mediated disease states effected thereby.

This invention further relates to a method of treating a human afflicted with a human immunodeficiency virus (HIV), which method comprises administering to a human in need of such treatment, an effective amount of a compound of Formula (I) or a pharmaceutically acceptable salt thereof.

Compounds of Formula (I) are useful in the treatment of additional viral infections, where such viruses are sensitive to upregulation by TNF, or will elicit TNF production in vivo.

DETAILED DESCRIPTION OF THE INVENTION

Definitions

As used herein, the following terms and expressions have the indicated meaning.

"Aryl" or "aralkyl", unless specified otherwise, means an aromatic ring or ring system of 6–10 carbon atoms, such as phenyl, benzyl, phenethyl, or naphthyl. The alkyl chain is meant to include both straight or branched chain radicals of 1 to 4 carbon atoms.

The term "$C_{1-2}$ alkyl", "$C_{1-4}$ alkyl", "$C_{1-6}$ alkyl" or "alkyl groups" includes both straight or branched chain radicals of 1 to 10 carbon atoms, unless the chain length is otherwise limited thereto, including, but not limited to methyl, ethyl, n-propyl, isopropyl, n-butyl, sec-butyl, isobutyl, tert-butyl, and the like.

The term "$C_{3-7}$ cycloalkyl" means groups of 3–7 carbon atoms, such as cyclopropyl, cyclopropylmethyl, cyclopentyl, or cyclohexyl.

"Cytokine" means any secreted polypeptide that affects the functions of cells, and is a molecule which modulates interactions between cells in immune, inflammatory, or hematopoietic responses. A cytokine includes, but is not limited to, monokines and lymphokines regardless of which cells produce them. The cytokine inhibited by the present invention for use in the treatment of an HIV-infected human must be a cytokine which is implicated in (a) the initiation and/or maintenance of T cell activation and/or activated T cell-mediated HIV gene expression and/or replication, and/or (b) any cytokine-mediated disease associated problem such as cachexia or muscle degeneration.

"Halo" includes all halogen radicals, i.e., chloro, fluoro, bromo, or iodo.

"Heteroaryl" means an aromatic ring system containing one or more heteroatoms, such as imidazolyl, triazolyl, oxazolyl, pyridyl, pyrimidyl, pyrazolyl, pyrrolyl, furanyl, or thienyl.

"Inhibiting the production of IL-1" or "inhibiting the production of TNF" means:

a) a decrease of excessive in vivo IL-1 or TNF levels in a human, to normal levels or below normal levels by inhibition of the in vivo release of IL-1 by all cells, including but not limited to monocytes or macrophages;

b) a down regulation, at the translational or transcriptional level, of excessive in vivo IL-1 or TNF levels in a human, to normal levels or below normal levels; or c) a down regulation, by inhibition of the direct synthesis of IL-1 or TNF levels as a postranslational event.

"Percentage" and "%" refers to percentage by weight of a component or ingredient based on the weight of the total composition containing such component or ingredient.

"TNF mediated disease or disease states" means any and all disease states in which TNF plays a role, either by production of TNF itself, or by TNF causing another cytokine to be released, such as but not limited to IL-1 or IL-6. A disease state in which IL-1, for instance, is a major component, and whose production or action is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are inhibited by the compounds of the present invention and thus are herein referred to collectively as "TNF" unless specifically delineated otherwise.

This invention relates to a method for mediating or inhibiting the enzymatic activity or catalytic activity of PDE IV in a mammal in need thereof and for inhibiting the production of TNF in a mammal in need thereof, which comprises administering to said mammal an effective amount of a compound of Formula (I) or a pharmaceutically acceptable salt thereof.

PDE IV inhibitors are useful in the treatment of a variety of allergic and inflammatory diseases, including: asthma, chronic bronchitis, atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and central nervous system disorders such as depression and multi-infarct dementia The viruses contemplated for treatment herein are those that produce TNF as a result of infection, or those which are sensitive to inhibition, such as by decreased replication, directly or indirectly, by the TNF inhibitors of Formula (I). Such viruses include, but are not limited to HIV-1, HIV-2 and HIV-3, cytomegalovirus (CMV), influenza, adenovirus and the Herpes group of viruses, such as, but not limited to, Herpes zoster and Herpes simplex.

This invention more specifically relates to a method of treating a mammal, afflicted with a human immunodeficiency virus (HIV), which comprises administering to such mammal an effective TNF inhibiting amount of a compound of Formula (I) or a pharmaceutically acceptable salt thereof.

The compounds of this invention may also be used in association with the veterinary treatment of animals, other than humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anemia virus, caprine arthritis virus, visna virus, maedi virus and other lentiviruses.

The compounds of this invention are also useful in treating yeast and fungal infections, where such yeast and fungi are sensitive to upregulation by TNF or will elicit TNF production in vivo. A preferred disease state for treatment is fungal meningitis. Additionally, a compound of Formula (I) may be administered in conjunction with other drugs of choice for systemic yeast and fungal infections. Drugs of choice for fungal infections, include but are not limited to the class of compounds called the polymycins, such as Polymycin B, the class of compounds called the imidazoles, such as clotrimazole, econazole, miconazole, and ketoconazole; the class of compounds called the triazoles, such as fluconazole, and itranazole, and the class of compounds called the Amphotericins, in particular Amphotericin B and liposomal Amphotericin B.

A compound of Formula (I) may also be used for inhibiting and/or reducing the toxicity of an anti-fungal, anti-bacterial or anti-viral agent by administering an effective amount of a compound of Formula (I) to a mammal in need of such treatment. Preferably, a compound of Formula (I) is administered for inhibiting or reducing the toxicity of the Amphotericin class of compounds, in particular Amphotericin B.

Preferred Compounds

The preferred compounds of this invention are those where $R_1$ is OH or —OCOH, X is $YR_2$ particularly where Y is O and $R_2$ is methyl substituted by 1 or more halogens; $R_3$ is CN or —C≡CH and Z is a carboxylic acid derivative such as a —C(O)OH, a salt thereof or an ester or amide derivative such as C(=Y')$R_{14}$, C(=O)O$R_{14}$, C(=Y')N$R_{10}R_{14}$, C(=N$R_{10}$)N$R_{10}R_{14}$. In addition, it is preferred that the $R_3$ group be axial and the Z group be equatorial.

The specific compounds disclosed herein are:

cis-{4-cyano-4-[3-(cis-3-hydroxycyclopentyloxy)-4-methoxyphenyl]cyclohexane-1-carboxylic acid};

cis-{-4-cyano-4-[3-(cis-3-formyloxycyclopentyloxy)-4-methoxyphenyl]cyclohexane-1-carboxylic acid}, and cis-{-4-cyano-4-[3-(trans-3-hydroxycyclopentyloxy)-4-methoxyphenyl]cyclohexane-1-carboxylic acid}.

Syntheses

Preparation of the compounds of Formula (I) can be carried out by one of skill in the art according to the procedures outlined reaction scheme set forth below and the specific chemistries set out in the Examples, infra. While the scheme and the examples illustrate the preparation of the cis/cis isomer(s), the cis/trans isomer(s) can be prepared by the same set of chemistries, with a nominal change in the treatment of compound 4; saponifying compound 4 provides the cis/trans compound namely the cis-{-4-cyano-4-[3-(trans-3-hydroxycyclopentyloxy)-4-methoxyphenyl] cyclohexane-1-carboxylic acid} or the corresponding compounds as defined by Formula I. The preparation of any remaining compounds of the Formula (I) not described therein may be prepared by the analogous processes disclosed herein which comprise:

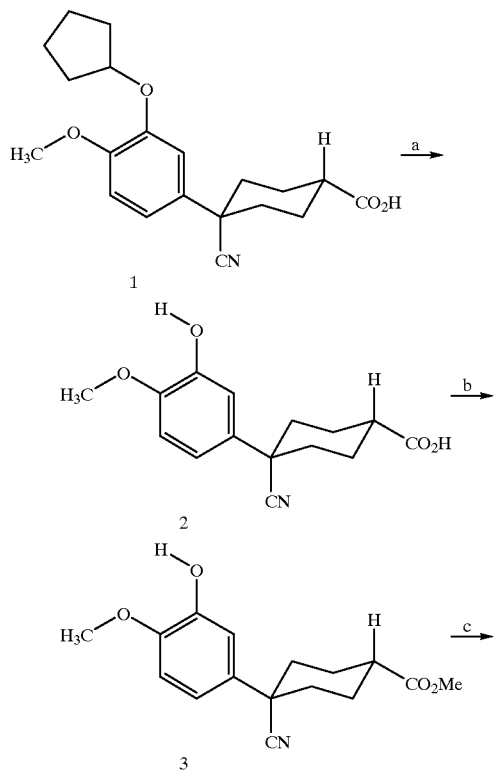

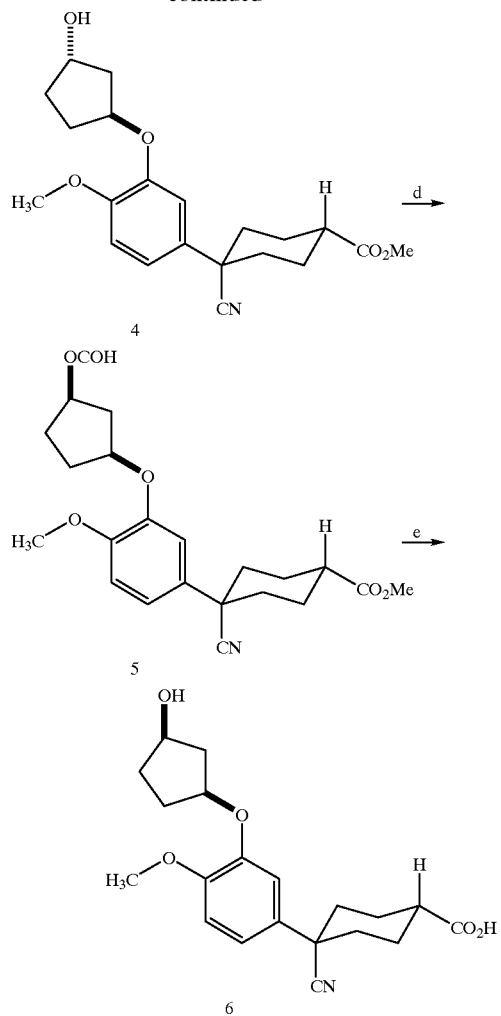

EXAMPLE 1

Preparation of cis-[4-cyano-4-(3-cyclopentyloxy-4-methoxyphenyl)cyclohexane-1-carboxylic acid]

1(a) (3-Cyclopentyloxy-4-methoxyphenyl)acetonitrile

To a solution of 3-cyclopentyloxy-4-methoxybenzaldehyde (20 g, 90.8 mmol) in acetonitrile (100 mL) was added lithium bromide (15 g, 173 mmol) followed by the dropwise addition of trimethylsilylchloride (17.4 mL, 137 mmol). After 15 min, the reaction mixture was cooled to 0° C., 1,1,3,3-tetramethyldisiloxane (26.7 mL, 151 mmol) was added dropwise and the resulting mixture was allowed to warm to room temperature. After stirring for 3 h, the mixture was separated into two layers. The lower layer was removed, diluted with methylene chloride and filtered through Celite®. The filtrate was concentrated under reduced pressure, dissolved in methylene chloride and refiltered. The solvent was removed in vacuo to provide a light tan oil. To a solution of this crude a-bromo-3-cyclopentyloxy-4-methoxytoluene in dimethylformamide (160 mL) under an argon atmosphere was added sodium cyanide (10.1 g, 206 mmol) and the resulting mixture was stirred at room temperature for 18 h, then poured into cold water (600 mL) and extracted three times with ether. The organic extract was washed three times with water, once with brine and was dried ($K_2CO_3$). The solvent was removed in vacuo and the residue was purified by flash chromatography (silica gel, 10% ethyl acetate/hexanes) to provide an off-white solid (m.p. 32–34° C.); an additional quantity of slightly impure material also was isolated.

1(b) Dimethyl 4-cyano-4-(3-cyclopentyloxy-4-methoxyphenyl)pimelate

To a solution of (3-cyclopentyloxy-4-methoxyphenyl) acetonitrile (7 g, 30.3 mmol) in acetonitrile (200 mL) under an argon atmosphere was added a 40% solution of Triton-B in methanol (1.4 mL, 3.03 mmol) and the mixture was heated to reflux. Methyl acrylate (27 mL, 303 mmol) was added carefully, the reaction mixture was maintained at reflux for 5 h and then cooled. The mixture was diluted with ether, was washed once with 1N hydrochloric acid and once with brine, was dried (MgSO$_4$) and the solvent was removed in vacuo. The solid residue was triturated with 5% ethanol/hexane to provide a white solid (m.p. 81–82° C.); an additional quantity was also obtained from the filtrate. Anal. (C$_{22}$H$_{29}$NO$_6$) calcd: C 65.49, H 7.25, N 3.47. found: C 65.47, H 7.11, N 3.49.

1(c) 2-Carbomethoxy-4-cyano-4-(3-cyclopentyloxy-4-methoxyphenyl)cyclohexan-1-one To a suspension of sodium methoxide (350 mL, 1.55 mol, 25% w/w in methanol) in toluene (2.45 L) heated to 80° C. under a nitrogen atmosphere was added a solution of dimethyl 4-cyano-4-(3-cyclopentyloxy-4-methoxyphenyl) pimelate (350.0 g, 0.87 mol) in toluene (1.05 L) over 10 min. The reaction was heated to 85° C. by distilling away 250 mL of solvent and was vigorously stirred under nitrogen for 2 hours. The reaction was cooled to 50° C. and was quenched with 3N (aq) HCl (700 mL, 2.1 mol). The organic layer was isolated, was washed once with deionized water (700 mL) and once with brine (700 mL). The organic layer was concentrated via low vacuum distillation to afford crude 2-carbomethoxy-4-cyano-4-(3-cyclopentyloxy-4-methoxyphenyl)cyclohexane-1-one in toluene. This was dissolved in 4.2 L of dimethyl sulfoxide and used in the next step.

1(d) 4-Cyano-4-(3-cyclopentyloxy-4-methoxyphenyl) cyclohexan-1-one

To a suspension of sodium chloride (315 g, 5.39 mol) and deionized water (315 mL) was added the dimethyl sulfoxide (4.2 L) solution of 2-carbomethoxy-4-cyano-4-(3-cyclopentyloxy-4-methoxyphenyl)cyclohexane-1-one ( 323 g, 0.87 mol) and the resulting suspension was heated to 155° C. for 1.75 h. The reaction was cooled to 40° C., was quenched into 8 L of iced water (2° C.) and was extracted with ethyl acetate (3.5 L). The aqueous layer was isolated and re-extracted with 2.5 L of ethyl acetate. The combined organic extract (6 L) was washed two times with deionized water (2×1 L) and once with brine (1 L). The organic layer was isolated and concentrated in vacuo to afford a residue. This residue was dissolved in refluxing isopropanol (500 mL), was cooled to 0° C. and held at this temperature for 1 hour. The crystals were isolated by filtration, were washed with 250 mL of isopropanol (0° C.), and were dried in a vacuum oven (45° C. at 20 inches) to produce 4-cyano-4-(3-cyclopentyloxy-4-methoxyphenyl)cyclohexan-1-one. m.p. 111–112° C.; Anal. (C$_{19}$H$_{23}$NO$_3$) calcd: C 72.82, H 7.40, N 4.47; found: C 72.72, H 7.39, N 4.48.

1(e) 2-[4-Cyano-4-(3-cyclopentyloxy-4-methoxyphenyl) cyclohexylidene]-1,3-dithiane To a solution of 2-trimethylsilyl-1,3-dithiane (9.25 mL, 48.7 mmol) in dry tetrahydrofuran (80 mL) at 0° C. under an argon atmosphere was added rapidly n-butyllithium (2.5M in hexanes, 19.2 mL, 48 mmol). After 10 min, the mixture was cooled to −78° C. and a solution of 4-cyano-4-(3-cyclopentyloxy-4-methoxyphenyl)cyclohexan-1-one (7.53 g, 23 mmol) in tetrahydrofuran (40 mL) was added. After 10 min, aqueous sodium chloride was added, the mixture was allowed to warm to room temperature and was diluted with water. This mixture was combined with the product of three substantially similar reactions conducted on ketone (3.04, 6.01 and 6.1 g, 48.3 mmol total), the combined mixture was extracted three times with methylene chloride, the extract was dried (MgSO$_4$) and evaporated. Purification by flash chromatography (silica gel, 10% ethyl acetate/hexanes) provided a white solid. m.p. 115–116° C.

1(f) cis-[4-Cyano-4-(3-cyclopentyloxy-4-methoxyphenyl) cyclohexane-1-carboxylic acid]

To a suspension of 2-[4-cyano-4-(3-cyclopentyloxy-4-methoxyphenyl)cyclohexylidene]-1,3-dithiane (140.0 g, 0.34 mol) in acetonitrile (500 mL) and deionized water (140 ml) under nitrogen was added trifluoroacetic acid (136 g, 1.19 mol). The suspension was heated to 65° C. for 1.25 h followed by the addition of 20% sodium hydroxide (420 g, 2.1 mol). The solution was heated at 70 to 75° C. for an additional 1.25 h, was cooled to 45° C., deionized water (420 ml)was added followed by 3N (aq) HCl (392 mL, 1.18 mol). The suspension was cooled to 5° C. and held for 1 h. The suspension was filtered, was washed with cold (5° C.) deionized water (200 mL), and was dried in a vacuum oven (40° C. at 20 inches) to obtain crude cis-[4-cyano-4-(3-cyclopentyloxy-4-methoxyphenyl)cyclohexane-1-carboxylic acid]. This material was assayed at 98.5% and was found to a 98.8:1.2 mixture of cis-to-trans isomers, which was contaminated with 0.1% of residual 1,3-propanedithiol. This material was purified via an oxidative workup as follows.

To a hot solution (65° C.) of crude cis-[4-cyano-4-(3-cyclopentyloxy-4-methoxyphenyl)cyclohexane-1-carboxylic acid] (85 g, 0.247 mol) in acetonitrile (425 mL) was added 1M sodium hydroxide (425 mL, 0.425 mol). To the solution (60° C.) was added 4.25 g of calcium hypochlorite and the suspension was vigorously stirred for 2 h. The reaction was concentrated by distilling out 320 mL of solvent, followed by the addition of ethyl acetate (425 mL). The reaction was again concentrated by distilling out 445 mL of solvent, was cooled to 55° C. followed by the addition of ethyl acetate (1.0 L) and 6N (aq.) HCl (100 mL). The organic layer was isolated, was washed three times with deionized water (3×300 mL), was filtered and was concentrated by distilling out 530 mL of solvent. To the solution was added ethyl acetate (635 mL) with continued distillation to remove 750 mL of solvent. The solution was cooled to 65° C. followed by the addition of hexane (340 mL). The suspension was cooled to 5° C., held at this temperature for 1 hour, was filtered and was washed with cold (5° C.) 10% ethyl acetate/hexane (200 mL). The solid was collected and was dried in a vacuum oven (40° C. at 20 inches) to obtain cis-[4-cyano-4-(3-cyclopentyloxy-4-methoxyphenyl) cyclohexane-1-carboxylic acid]. This material was found to contain no trans isomer. Anal.(C$_{20}$H$_{25}$NO$_4$) calcd: C 69.95, H 7.34, N 4.08; found: C 69.90, H 7.35, N 4.02.

EXAMPLE 2

Preparation of cis-{4-cyano-4-[3-(trans-3-hydroxycyclopentyloxy)-4-methoxyphenyl]-cyclohexane-1-carboxylic acid}

2(a) cis-[4-Cyano-4-(3-hydroxy-4-methoxyphenyl) cyclohexane-1-carboxylic acid]

To a solution of boron tribromide in dichlororrmethane (0.1M, 335 mL, 33.5 mmol) under an argon atmosphere at −78° C. was slowly added a solution of cis-[4-cyano-4-(3-cyclopentyloxy-4-methoxyphenyl)cyclohexane-1-carboxylic acid] (4.03 g, 11.7 mmol) in dichloromethane (180 mL). The mixture was stirred for 5 min, 15% sodium methoxide in methanol was added to pH 8–9 and the reaction was warmed to RT. Water (100 mL) was added and the mixture was acidified with 3N aqueous hydrochloric acid to pH 1–2. The organic layer was separated, was dried (MgSO$_4$/Na$_2$SO$_4$), was filtered and was evaporated. The residue was twice dissolved in chloroform and the solution was evaporated to yield a white solid. $^1$H NMR(400 MHz, CDCl$_3$) δ 7.01 (d, J=2.4 Hz, 1H), 6.96 (d of d, J=2.4, 8.5 Hz, 1H), 3.89 (s, 3H), 2.31 (m, 1H), 2.21 (br t, J=13.6 Hz, 4H), 1.98 (m,2H), 1.77 (m, 2H); mp 190–193° C.

2(b) Methyl cis-[-4-cyano-4-(3-hydroxy-4-methoxyphenyl) cyclohexane-1-carboxylate]

p-Toluenesulfonic acid monohydrate (0.015 g, 0.08 mmol) was added to a solution of the compound of Example 2(a) (0.70 g, 2.54 mmol) in dry methanol (20 mL) under an argon atmosphere and the reaction was stirred for 6 h at 45–50° C. The reaction was cooled to RT and was stirred for an additional 16 h. The solution was evaporated and the residue was purified by flash chromatography (silica gel, 50% hexane/ethyl acetate) to yield the title compound as a white solid. $^1$H NMR(400 MHz, CDCl$_3$) δ 7.01 (m, 2H), 6.85 (d, J=9.1 Hz, 1H), 3.90 (s, 3H), 3.72 (s, 3H), 2.35 (t of t, J=3.6, 12.2 Hz, 1H), 2.14–2.25 (m, 4H), 2.00 (app q, J=13.4 Hz, 1H), 1.99 (app q, J=13.4 Hz, 1H), 1.77 (app t, J=13.4 Hz, 1H), 1.76 (app t, J=13.4 Hz, 1H); mp 106–107° C.

2(c) Methyl cis-{-4-cyano-4-[3-(trans-3-hydroxycyclopentyloxy)-4-methoxyphenyl]-cyclohexane-1-carboxylate}

The compound of Example 2(b) (0.69 g, 2.37 mmol) was dissolved in tetrahydrofuran (20 mL) under an argon atmosphere and was treated with triphenylphosphine (1.24 g, 4.74 mmol) and cis-1,3-cyclopentanediol (0.49 g, 4.74 mmol). Diethyl azodicarboxylate (0.83 g, 4.74 mmol) was added and the mixture was stirred at RT for 16 h. The solution was evaporated, the residue was diluted with ether and the white solid was removed by filtration. The filtrate was concentrated and the residue was purified by flash chromatography (silica gel, 50% hexane/ethyl acetate) to yield a mixture of the title compound and triphenylphosphine oxide. The mixture was diluted with ether and the white solid triphenylphosphine oxide was removed by filtration. Evaporation of the filtrate yielded the tide compound as a sticky, colorless semi-solid. $^1$H NMR(400 MHz, CDCl$_3$) δ 7.07 (d, J=2.4 Hz, 1H), 7.02 (d of d, J=2.4, 8.8 Hz, 1H), 6.87 (d, J=8.8 Hz, 1H), 4.99 (m, 1H), 4.37 (m, 1H), 3.85 (s, 3H), 3.74 (s, 3H), 3.16 (d, J=9.1 Hz, 1H), 2.39 (m, 1H), 1.88–2.25 (m, 12H), 1.80 (br t, J=13.5 Hz, 2H).

2(d) cis-{-4-cyano-4-[3-(trans-3-hydroxycyclopentyloxy)-4-methoxyphenyl]cyclohexane-1-carboxylic acid}

The compound of Example 2(c) (0.10 g, 0.27 mmol) was dissolved in 5:5:2 tetrahydrofuran/methanol/water (5 mL), sodium hydroxide (0.035 g, 0.88 mmol) was added and the mixture was stirred at RT for 3 h. The solvent was evaporated, the residue was partitioned between 5% aqueous NaOH and dichloromethane and the layers were separated. The aqueous layer was acidified to pH 3 with 3N aqueous hydrochloric acid and was extracted three times with 5% methanol in chloroform. The organic extracts were combined, were dried (MgSO4), filtered and evaporated. The residue was purified by flash chromatography (silica gel, 90:10:1 chloroform/methanol/water) to yield a solid which was slurried in ether, was collected by filtration and was dried in vacuo to afford the title compound. MS(CI/NH$_3$) m/e 377 [M+NH$_3$]+; $^1$H NMR(400 MHz, CDCl$_3$) δ 7.08 (br s, 1H), 7.03 (br d, J=8.5Hz, 1H), 6.88 (d, J=8.5 Hz, 1H), 4.98 (m, 1H), 4.38 (m, 1H), 3.84 (s, 1H), 2.41 (m, 1H), 1.77–2.29 (m, 16H); Anal. (C$_{20}$H$_{25}$NO$_5$·0.9 H$_2$O) calcd: C, 63.95; H,7.19; N,3.73. found: C, 64.06; H, 6.88; N, 3.77; mp 161–163° C.

EXAMPLE 3

Preparation of cis-{4-cyano-4-[3-(cis-3-hydroxycyclopentyloxy)-4-methoxyphenyl]-cyclohexane-1-carboxylic acid}

3(a) Methyl cis-{-4-cyano-4-[3-(cis-3-formyloxycyclopentyloxy)-4-methoxyphenyl]-cyclohexane-1-carboxylate}

The compound of Example 2(c) (0.68 g, 1.83 mmol) was dissolved in tetrahyrofuran (20 mL) under an argon atmosphere and was treated with triphenylphosphine ( 0.96 g, 3.66 mmol) and formic acid (0.17 g, 3.66 mmol). Diethyl azodicarboxylate (0.64 g, 3.66 mmol) was added and the mixture was stirred at RT for 16 h. The solution was evaporated, ether was added and the white solid was removed by filtration. The filtrate was concentrated and the residue was purified by flash chromatography (silica gel, 65% hexane/ethyl acetate) to yield the title compound as a clear colorless oil. $^1$H NMR(400 MHz, CDCl$_3$) δ 8.02 (s,1H), 7.0 (d of d, J=2.4, 8.2 Hz, 1H), 6.99 (d, J=2.4 Hz, 1 H), 6.87 (d, J=8.2 Hz, 1H), 5.48 (m, 1H), 4.95 (m, 1H), 3.84 (s, 3H), 3.72 (s, 3H), 2.31–2.40 (m, 2H), 2.13–2.28 (m, 7H), 1.96–2.06 (m, 3H), 1.74–1.87 (m, 3H).

3(b) cis-{-4-cyano-4-[3-(cis-3-hydroxycyclopentyloxy)-4methoxyphenyl]cyclohexane-1-carboxylic acid}

The compound of Example 3(a) (0.52 g, 1.31 mmol) was dissolved in 5:5:2 tetrahydrofuran/methanol/water (20mL), sodium hydroxide (0.32 g, 8.0 mmol) was added and the mixture was stirred at RT for 2.5 h. The solvent was evaporated and the aqueous residue was acidified to pH 1–2 with 3N aqueous hydrochloric acid. The white solid product was collected, was washed with water and was dried in vacuo to afford the title compound as a white solid. MS(CI/NH$_3$) m/e 377 [M+NH3]+; 1H NMR(250 MHz, CDCl$_3$) δ 6.98 (m, 2H), 6.86 (d, J=8.2 Hz, 1H), 4.97 (m, 1H), 4.59 (m, 1H), 3.85 (s, 3H), 1.64–2.47 (m, 17H); mp 143–145° C.

METHODS OF TREATMENT

In order to use a compound of Formula (I) or a pharmaceutically acceptable salt thereof may be used neat though a preferred technique is to present them with a carrier/diluent accordance with standard pharmaceutical practice. Any formulation compatible with the chosen method of delivery and the stability of the compound may be used. One skilled in the art will be able to select and prepare an acceptable formulation in accordance with standard practices in the field of the formulary arts.

The compounds of Formula (I) or may be administered orally (when active by this route), oral, intravenous, intraperitoneal, and intramuscular administration, topically, parenterally, or by inhalation in conventional dosage forms prepared by combining such agent with standard pharmaceutical carriers according to conventional procedures in an amount sufficient to produce the desired therapeutic activity.

The amount of a compound of Formula (I) required for therapeutic effect on topical administration will, of course, vary with the compound chosen, the nature and severity of the condition and the animal undergoing treatment, and is ultimately at the discretion of the physician.

The daily dosage regimen for oral administration is suitably about 0.001 mg/kg to 100 mg/kg, preferably 0.01 mg/Kg to 40 mg/Kg, of a compound of Formula (I) or a pharmaceutically acceptable salt thereof calculated as the free base. The active ingredient may be administered from 1 to 6 times a day, sufficient to exhibit activity.

UTILITY EXAMPLES

Example A

Inhibitory effect of compounds of Formula (I) on in vitro TNF production by human monocytes The inhibitory effect of compounds of Formula (I) on in vitro TNF production by human monocytes may be determined by the protocol as described in Badger et al., EPO published Application 0 411 754 A2, Feb. 6, 1991, and in Hanna, WO 90/15534, Dec. 27, 1990.

Example B

Two models of endotoxic shock have been utilized to determine in vivo TNF activity for the compounds of Formula (I). The protocol used in these models is described in Badger et al., EPO published Application 0 411 754 A2, Feb. 6, 1991, and in Hanna, WO 90/15534, Dec. 27, 1990.

The exemplified compounds herein demonstrated a positive in vivo response in reducing serum levels of TNF induced by the injection of endotoxin.

Example C

Isolation of PDE Isozymes

The phosphodiesterase inhibitory activity and selectivity of the compounds of Formula (I) can be determined using a battery of five distinct PDE isozymes. The tissues used as sources of the different isozymes are as follows: 1) PDE Ib, porcine aorta; 2) PDE Ic, guinea-pig heart; 3) PDE III, guinea-pig heart; 4) PDE IV, human monocyte; and 5) PDE V (also called "Ia"), canine trachealis. PDEs Ia, Ib, Ic and III are partially purified using standard chromatographic techniques [Torphy and Cieslinski, *Mol. Pharmacol.*, 37:206–214, 1990]. PDE IV is purified to kinetic homogeneity by the sequential use of anion-exchange followed by heparin-Sepharose chromatography [Torphy et al., J. Biol. Chem., 267:1798–1804, 1992].

Phosphodiesterase activity is assayed as described in the protocol of Torphy and Cieslinski, *Mol. Pharmacol.*, 37:206–214, 1990. Positive $IC_{50}$'s in the nanomolar to $\mu M$ range for compounds of the workings examples described herein for Formula (I) have been demonstrated.

Example D

The ability of selected PDE IV inhibitors to increase cAMP accumulation in intact tissues is assessed using U-937 cells, a human monocyte cell line that has been shown to contain a large amount of PDE IV. To assess the activity of PDE IV inhibition in intact cells, nondifferentiated U-937 cells (approximately $10^5$ cells/reaction tube) were incubated with various concentrations (0.01–1000 $\mu M$) of PDE inhibitors for one minute and 1 $\mu M$ prostaglandin E2 for an additional four minutes. Five minutes after initiating the reaction, cells were lysed by the addition of 17.5% perchloric acid, the pH was neutralized by the addition of 1 M potassium carbonate and cAMP content was assessed by RIA. A general protocol for this assay is described in Brooker et al., Radioimmunassay of cyclic AMP and cyclic GMP., Adv. Cyclic Nucleotide Res., 10:1–33, 1979. The compounds of the working examples as described herein for Formula (I) have demonstrated a positive $EC_{50}$s in the $\mu M$ range in the above assay.

No toxic effects are expected when these compounds are administered in accordance with the present invention.

What is claimed is:
1. A compound of Formula I

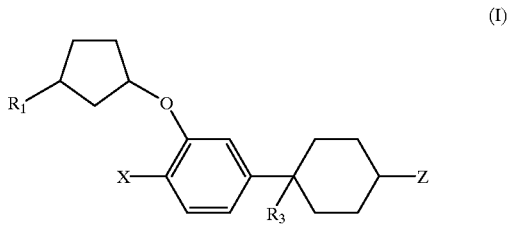

wherein
$R_1$ is OH or an ether or ester thereof,
X is $YR_2$, halogen, nitro, $NR_4R_5$ or formyl amine;
Y is O or $S(O)_m$, where m is 0, 1 or 2;
$R_2$ is methyl or ethyl, where either methyl or ethyl may be optionally substituted by 1 or more halogens;
$R_3$ is hydrogen, halogen, $C_{1-4}$alkyl, $CH_2NHC(O)C(O)NH_2$, halo-substituted $C_{1-4}$alkyl, —CH=CHR$_8$·R$_8$·, cyclopropl optionally subsituted by $R_{8'}$, CN, $OR_8$, $CH_2OR_8$, $NR_8R_{10}$, $CH_2NR_8R_{10}$, C(Z')H, $C(O)OR_8$, $C(O)NR_8R_{10}$, or —C≡C$R_8$;
$R_4$ and $R_5$ are independently hydrogen or $C_{1-2}$ alkyl;
$R_7$ is —$(CR_4R_5)_qR_{12}$ or $C_{1-6}$ alkyl wherein the $R_{12}$ or $C_{1-6}$ alkyl group is optionally substituted one or more times by $C_{1-2}$ alkyl optionally substituted by one to three groups selected from —F, —Br, —Cl, —$NO_2$, —$NR_{10}R_{11}$, —C(=O)$R_8$, —C(=O)$OR_8$, —$OR_8$, —CN, —C(=O)$NR_{10}R_{11}$, —OC(=O)$NR_{10}R_{11}$, —OC(=O)$R_8$, —$NR_{10}C(=O)NR_{10}R_{11}$, —$NR_{10}C(=O)R_{11}$, —$NR_{10}C(=O)OR_9$, —$NR_{10}C(=O)R_{13}$, —C(=$NR_{10})NR_{10}R_{11}$, —C(=N—CN)$NR_{10}R_{11}$, —C(=N—CN)$SR_9$, —$NR_{10}C(=N—CN)NR_{10}R_{11}$, —$NR_{10}S(=O)_2R_9$, —$S(O)_mR_9$, —$NR_{10}C(=O)C(=O)NR_{10}R_{11}$, —$NR_{10}C(=O)C(=O)R_{10}$, thiazolyl, imidazolyl, oxazolyl, pyrazolyl, triazolyl or tetrazolyl;
$R_8$ is —H or $R_9$;
$R_{8'}$ is $R_8$ or fluorine;
$R_9$ is $C_{1-4}$ alkyl optionally substituted by one to three —F;
$R_{10}$ is $OR_8$, hydrogen, or $C_{1-4}$alkyl optionally substituted by one to three fluorines;
$R_{11}$ is —H or $C_{1-4}$ alkyl optionally substituted by one to three —F; or when $R_{10}$ and $R_{11}$ are as $NR_{10}R_{11}$ they may together with the nitrogen form a 5 to 7 membered ring optionally containing at least one additional heteroatom selected from O, N or S;
$R_{12}$ is $C_{3-7}$ cycloalkyl, 2-pyridyl, 3-pyridyl, 4-pyridyl, pyrimidyl, pyrazolyl, 1-imidazolyl, 2-imidazolyl, thiazolyl, triazolyl, pyrrolyl, piperazinyl, piperidinyl, morpholinyl, furanyl, 2-thienyl, 3-thienyl, 4-thiazolyl, 5-thiazolyl, quinolinyl, naphthyl or phenyl;
$R_{13}$ is a heterocyclic ring selected from oxazolidinyl, oxazolyl, thiazolyl, pyrazolyl, triazolyl, tetrazolyl, imidazolyl, imidazolidinyl, thiazolidinyl, isoxazolyl, oxadiazolyl or thiadiazolyl, where $R_{13}$ is appended to a compound of Formula (I) through a carbon atom of the heterocyclic ring, and where each heterocyclic ring may be unsubstituted or substituted by one or two $C_{1-2}$ alkyl groups;
$R_{14}$ is H or $R_7$, or when $R_{10}$ and $R_{14}$ are as $NR_{10}R_{14}$, they may together with the nitrogen atom form a 5 to 7 membered ring optionally containing at least one additional heteroatom selected from O, N or S;

m' is 0, 1 or 2;

q is 0, 1 or 2.

Y' is O or S;

Z is C(=Y')$R_{14}$, C(=O)O$R_{14}$, C(=Y')N$R_{10}R_{14}$, C(=N$R_{10}$)N$R_{10}R_{14}$, CN, C(=NO$R_8$)$R_{14}$, C(=O)N$R_8$N$R_8$C(=O)$R_8$, C(=O)N$R_8$N$R_{10}R_{14}$, C(=NO$R_{14}$)$R_8$, C(=N$R_8$)N$R_{10}R_{14}$, C(=N$R_{14}$)N$R_8R_8$, C(=N—CN)N$R_{10}R_{14}$, C(=N—CN)S$R_9$, 2-imidazolyl, 4-imidazolyl, 5-imidazolyl, 3-pyrazolyl, 4-pyrazolyl, 5-pyrazolyl, 4-triazolyl[1,2,3], 5-triazolyl[1,2,3], 3-triazolyl[1,2,4], 5-triazolyl[1,2,4], 5-tetrazolyl, 2-oxazolyl, 4-oxazolyl, 5-oxazolyl, 3-isoxazolyl, 4-isoxazolyl, 5-isoxazolyl, 3-oxadiazolyl[1,2,4], 5-oxadiazolyl[1,2,4], 2-oxadiazolyl[1,3,4], 2-thiadiazolyl[1,3,4], 2-thiazolyl, 4-thiazolyl, 5-thiazolyl, 2-oxazolidinyl, 4-oxazolidinyl, 5-oxazolidinyl, 2-thiazolidinyl, 4-thiazolidinyl or 5-thiazolidinyl, 2-imidazolidinyl, 4-imidazolidinyl, or 5-imidazolidinyl; wherein all of the heterocyclic ring systems may be optionally substituted one or more times by $R_{14}$;

Z' is O, N$R_9$, NO$R_8$, NCN, C(—CN)$_2$, C$R_8$CN, C$R_8$NO$_2$, C$R_8$C(O)O$R_8$, C$R_8$C(O)N$R_8R_8$, C(—CN)NO$_2$, C(—CN)C(O)O$R_9$, or C(—CN)C(O)N$R_8R_8$; or a pharmaceutically acceptable salt thereof.

2. A compound of claim 1 wherein $R_1$ is OH or —OCOH, X is Y$R_2$, Y is O, $R_2$ is methyl substituted by 1 or more halogens; $R_3$ is CN or —C≡CH, Z is a carboxylic acid derivative such as a —C(O)OH, a salt thereof or an ester or amide derivative such as C(=Y')$R_{14}$, C(=O)O$R_{14}$, C(=Y')N$R_{10}R_{14}$, C(=N$R_{10}$)N$R_{10}R_{14}$ and the $R_3$ group is axial and the Z group is equatorial.

3. A compound of claim 2 which is
   cis-{4-cyano-4-[3-(cis-3-hydroxycyclopentyloxy)-4-methoxyphenyl]cyclohexane-1-carboxylic acid};
   cis-{-4-cyano-4-[3-(cis-3-formyloxycyclopentyloxy)-4-methoxyphenyl]cyclohexane-1-carboxylic acid}, or
   cis-{-4-cyano-4-[3-(trans-3-hydroxycyclopentyloxy)4-methoxyphenyl]cyclohexane-1-carboxylic acid}, or a pharmaceutically acceptable salt thereof.

4. A method for treating asthma comprising a compound according to claim 1 and a pharmaceutically acceptable excipient.

5. A pharmaceutical composition comprising a compound of according to claim 1.

6. A process for preparing an acid of formula IV

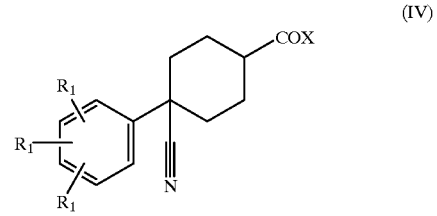

(IV)

wherein $R_1$ is hydrogen or another substituent and X is OH or a salt thereof or —O—$C_{1-6}$alkyl, which process comprises hydrolyzing a thioketene of formula (C)

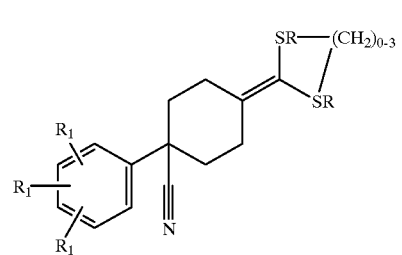

C where R is hydrogen using an acid and aqueous solvent system and heating the mixture to between 40 and 80° C. for 30 minutes to 2 hours, and then adding a base.

7. The process of claim 6 wherein the base is an alkali metal alkoxide.

8. The process of either claim 6 or 7 wherein the acid is trifluoroacetic acid.

9. The process of any one of claims 6 to 8 wherein the product is an acid of formula IV which is cis-[4-cyano-4-(3-cyclopentyloxy-4-methoxyphenyl)cyclohexane-1-carboxylic acid] or a salt thereof.

* * * * *